United States Patent [19]

Goedecke

[11] Patent Number: 4,807,484

[45] Date of Patent: Feb. 28, 1989

[54] APPARATUS FOR THE MEASUREMENT AND NON-DESTRUCTIVE MATERIAL TESTING OF LAID PIPELINES

[75] Inventor: Hartmut Goedecke, Weilburg, Fed. Rep. of Germany

[73] Assignee: Kernforschungszentrum Karlsruhe GmbH and Pipetronix GmbH, Karlsruhe, Fed. Rep. of Germany

[21] Appl. No.: 82,214

[22] Filed: Aug. 6, 1987

[30] Foreign Application Priority Data

Aug. 6, 1986 [DE] Fed. Rep. of Germany ....... 3626646

[51] Int. Cl.⁴ ................................. G01B 5/28
[52] U.S. Cl. .................................... 73/865.8; 73/866.5
[58] Field of Search ...................... 73/866.5, 865.8, 623

[56] References Cited

U.S. PATENT DOCUMENTS

| | | | |
|---|---|---|---|
| 4,098,126 | 7/1978 | Howard | 73/866.5 |
| 4,342,225 | 8/1982 | Jandera et al. | 73/865.8 |
| 4,457,073 | 7/1984 | Payne | 73/866.5 |

Primary Examiner—Stewart J. Levy
Assistant Examiner—Robert P. Bell
Attorney, Agent, or Firm—Antonelli, Terry & Wands

[57] ABSTRACT

An apparatus for the measurement and non-destructive material testing of laid pipelines in the form of a scraper moved through the pipeline and guided on the inner wall thereof, has at least one circular support with sensors arranged on the circumference thereof and at least one pressure-tight casing, which has devices for processing and recording the measured values and the power supply. In order to ensure that the sensors are always at the minimum constant distance and with a constant angular position with respect to the pipe wall, the support is constructed as a cylindrical sleeve made from a rubber elastic material and is provided with an axially, radially and circumferentially regular profile, whose protuberances are located on a cylindrical envelope surface with a somewhat larger external diameter than the internal diameter of the pipeline and in whose depressions the sensors are arranged on a surface concentric to the envelope surface. The sleeve is attached by universal joint to the trailing end of the scraper.

17 Claims, 8 Drawing Sheets

APPARATUS FOR THE MEASUREMENT AND NON-DESTRUCTIVE MATERIAL TESTING OF LAID PIPELINES

BACKGROUND OF THE INVENTION

The present invention relates to an apparatus for the measuring and non-destructive material testing of laid pipelines in the form of a scraper moved through the pipeline and guided on the inner wall thereof and which has at least one circular support with sensors arranged on its circumference and at least one pressure-tight casing, which receives devices for processing and recording the measured values, as well as for the power supply.

Apparatuses of this type, which are also called intelligent scrapers, are increasingly being used in long-distance pipelines, particularly for transporting oil and gas for the purpose of detecting faults on said pipeline. They are generally moved through the pipeline by the medium transported and perform measurements of different types. It is most frequently a question of carrying out measurements on the pipe wall, so as to be able to e.g. establish local corrosion, wall thickness reductions due to mechanical damage, pitting and the like. Differently functioning sensors are used as a function of the intended task, e.g. electrooptical, ultrasonic and similar sensors.

In order to scan the entire circumference of the pipe wall, the sensors are arranged on a rigid ring (U.S. Pat. No. 4,022,055), whereby the ring and, therefore, also the sensors must have a significant distance from the pipe wall, so as not to be damaged by non-circularities of the pipe or local bulges. The measuring accuracy suffers as a result of the significant distance between the effective areas of the sensors and the pipe wall. The measurement result is also falsified in the case of non-circularities and bulges, due to the different type of spacing conditions at the points. In addition, rotary supports for sensors are known (DE-OS No. 2 156 434 and U.S. Pat. No. 3,539,915), but as a result of the rotary movement constitute a source of additional operational problems. Moveover, the sensors are connected by complicated mechanical articulations, linkages, etc to the rotary support, which are intended to ensure that the sensors are guided at a constant distance from the inner wall of the pipe. However, these mechanical means additionally impair the operational reliability. Here again a constant distance between effective sensor area and pipe wall is only ensured to a limited extend. In particular the angulr position of the sensor with respect to the pipe wall, which should always be perpendicular, is not ensured, particularly in the case of non-circularity or other bulges on the pipeline. In addition, a surface-covering scanning is only possible with significant expenditure and effort, if at all, so that in certain circumstances small local defects may not be detected.

SUMMARY OF THE INVENTION

The aim underlying the present invention resides in providing an apparatus with a simple and operationally reliable construction, in which the distance between the sensors and the pipe wall is relatively small and identical for all the sensors and neither the distance, nor the angular position of the sensors with respect to the pipe wall are modified by non-circularities thereof.

According to the invention the support is constructed as a cylindrical sleeve made from rubber elastic material and is provided with a regular profile in the axial, radial and circumferential direction, whose protuberances are located on a cylindrical envelope surface having a somewhat larger external diameter than the internal diameter of the pipeline and in whose depressions the sensors are arranged on a surface concentric to the envelope surface.

The invention proposes a sensor support in the form of a sleeve made from a material with rubber elastic characteristics, which can consequently adapt to the pipe wall, particularly to unevennesses. In the relaxed starting position the sleeve or envelope surface of the profile protuberances has a somewhat larger external diameter than the internal diameter of the pipeline. On inserting in the pipeline the sleeve is somewhat circumferencially compressed, so that the profile protuberances snugly engage on the pipe wall and this is still ensured when the pipeline has non-circularities, bulges and the like. The sensors are located in the profile depressions on a surface concentric to the envelope surface and, consequently, have an identical, clearly defined spacing, as well as an identical and clearly defined angular position with respect to the pipe wall. As the sleeve and, consequently, also the profile depressions follow any non-circularities of the pipe, the spacing and angular position of the sensors with respect to the pipe wall also remain identical at these point. Thus, a completely satisfactory operation of the sensors is ensured over the entire measuring distance or range. It is a decisive advantage compared with the known scrapers with sensors guided in a spacing-variable manner, that the inventive apparatus has no moving parts and no mechanical transmission elements, so that an operationally reliable apparatus is obtained, which is of decisive importance when working within a pipeline over long distances.

According to a preferred construction the protuberances and depressions are constructed in or axially extending manner. Thus, in cross section, the sleeve has a profile giving it a good reversible deformability in the circumferential direction while through it substantially axially parallel extension it leads to no significant increase in the resistance in the direction of movement of the scraper.

Advantageously the depressions are formed by grooves in the cylindrical sleeve, the latter being preferably provided in the vicinity of the protuberances with substantially axially parallel grooves. Thus, circumferentially, the sleeve has a type, of concertina profile, which further favors the reversible deformability and deflects the forces acting on the sleeve mainly in the circumferential direction, so that such radial forces substantially lead to a reduction or increase in the diameter. This also ensures that the sensors always retain their spacing and angular position with respect to the pipe wall. This profile ensures the deformability of the sleeve also in the longitudinal direction, so that in all it is well adapted to radially and axially extending non-circularities in the pipeline.

In the vicinity of both the protuberances and the depressions, the profile can have a relatively large wall thickness, so as to externally prevent the wear necessarily occurring due to the guidance in the pipeline and so as to internally have an adequate carrying strength for receiving the sensors. However, the substantially radially directed wall webs between the protuberances and the depressions can be in a relatively thin-walled form and, therefore, further aid deformability.

In place of the grooves provided on the inside in the vicinity of the strip-like protuberances, in the vicinity of the latter the sleeve can also be provided with a narrow pattern of small diameter holes, so that in this area the sleeve has increased transverse compressibility. It can virtually "breath" in the vicinity of the protuberances and in particular gives or yields in the circumferential direction, whereas, the profile is dimensionally stable in the vicinity of the strip-like depressions.

According to a preferred construction of the invention the protuberances and groove-like depressions are arranged at an acute angle to the sleeve axis. If several sensors are successively arranged in these grooves, then between the sensors there is a mutual circumferential displacement, so that the sensors arranged in one groove cover one surface strip on the pipe wall which is wider than the effective area of each individual sensor.

Preferably, the angle between the axial direction of the groove-like depressions and the axis of the sleeve is such that the active areas of the sensors successively arranged in the depression overlap one another, when considered axially. This permits a surface-covering scanning or measurement on the pipe wall.

This is also the purpose served by the further measure, according to which the length of the groove-like depressions is such that the effective area of the last sensor in one depression and the first sensor in the adjacent depression overlap one another. The length of the groove-like depressions necessary for a surface-covering inspection of the pipeline and therefore the length of the sleeve is mainly determined by the size of the angle at which the depressions are set with respect to the axial direction.

In order to position the sensors, the sleeve has threaded bushes open towards the inside for threadably mounting the sensors and which are advantageously arranged on the material strip of the sleeve forming the groove-like depressions between the holes receiving the sensors.

According to another development of the invention, on the end of the sleeve in advance in the movement direction of the scraper, it is drawn conically inwardly to form a support flange by which it is fixed to the scraper. The conically drawn end face leads the sleeve over any obstacles in the pipeline.

The inventively constructed apparatus is optimized according to another feature of the invention in that the sleeve is joined to the scraper by a central universal joint, with the sleeve preferably being attached to the end of the scraper which trails in the direction of movement. As a result of this construction the apparatus is drawn by the scraper, in much the same way as a two-wheel trailer, and as a result of the cardan joint, the sleeve follows the pipe wall when the pipe bends and the angular deviation between pipe axis and sleeve axis is kept to a minimum. Advantageously the cardan joint is located at a limited distance behind the guide rolls engaging on the pipe wall and provided on the trailing end of the scraper.

Preferably, between the cardan joint and the support flange of the sleeve, are provided a plurality of tie rods distributed about the axis and spherically mounted at both ends. As a result of this construction the sleeve remains flexible in its support flange and gives way to non-circularities in the pipe in impediment-free manner. In addition, the sleeve can constantly center itself without being forced out of the pipe axis by movements of the scraper.

According to an appropriate embodiment at the end of the tie rods facing the scraper they are spherically mounted on an intermediate plate, which, in turn, has the cardan joint.

Finally, the tie rods slope outwardly from the intermediate plate and preferably extend somewhat in the axial direction of the drawn conical portion of the sleeve. Thus, the tensil forces act in the direction of the conical portion of the sleeve, so that deformations in a vicinity of the support flange of the sleeve are avoided.

BRIEF DESCRIPTION OF THE DRAWINGS

The invention is described in greater detail hereinafter relative to non-limitative embodiments and the attached drawings, wherein.

DETAILED DESCRIPTION OF THE PREFERRED EMBODIMENTS

Figure 1:
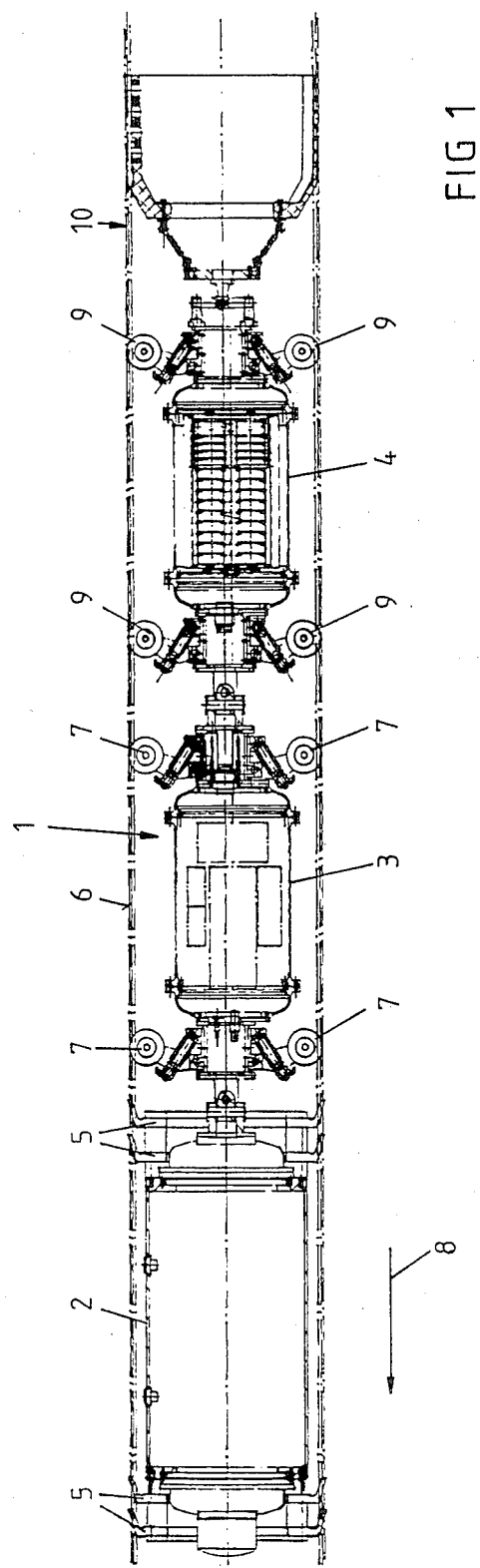
FIG. 1 is a side view of an embodiment of the scraper.

In the embodiment shown in FIG. 1, the scraper has three successively arranged scraper bodies 2, 3, 4, with, in each case, a pressure-tight casing. The casing of the first scraper body 2 is provided with several sleeves 5, which internally tightly engage with the pipeline 6 and ensure the advance of scraper 1 with the aid of the medium transported in the pipeline. The casing of scraper body 2 contains e.g. batteries for the electric power supply of the apparatus. The second scraper body 3 is guided on the inner wall of pipeline 6 by front and rear roller sets 7 and receives in its casing the data processing and recording devices, while the last scraper body 4 in the apparatus movement direction 8 contains in its casing test electronics for the hereinafter described sensors. This scraper body 4 is also guided on the inner wall of pipeline 6 by roller sets 9. In the embodiment shown in FIG. 1, a sleeve generally designated by the reference numeral 10 with the sensors is attached to the trailing end of the scraper 1.

Figure 2:
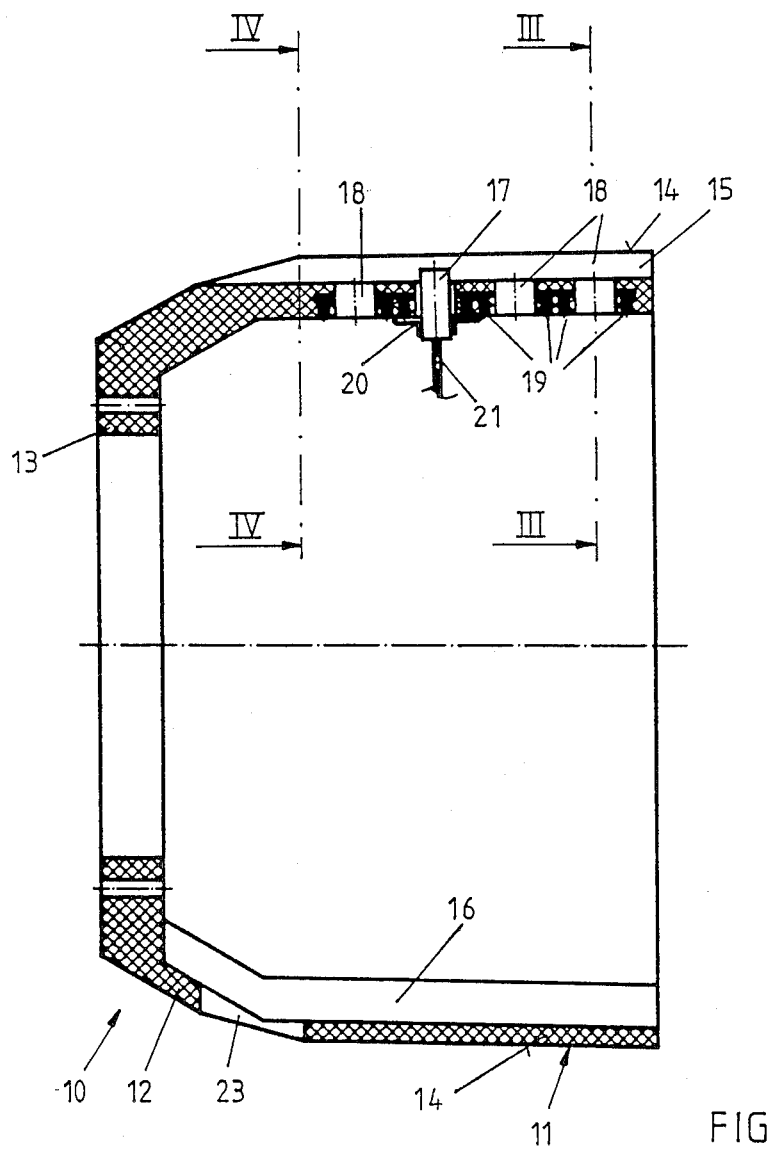
FIG. 2 is a larger-scale longitudinal section through an embodiment of the sleeve.

FIG. 2 shows sleeve 10 made from a rubber elastic material in longitudinal section. It has a cylindrical, hose-like portion 11, which is drawn inwards by a conical portion 12 at its leading end in the movement direction 8 of scraper 1. Conical portion 12 passes into a support flange 13, by which sleeve 10 is fixed to scraper 1.

Figure 3:
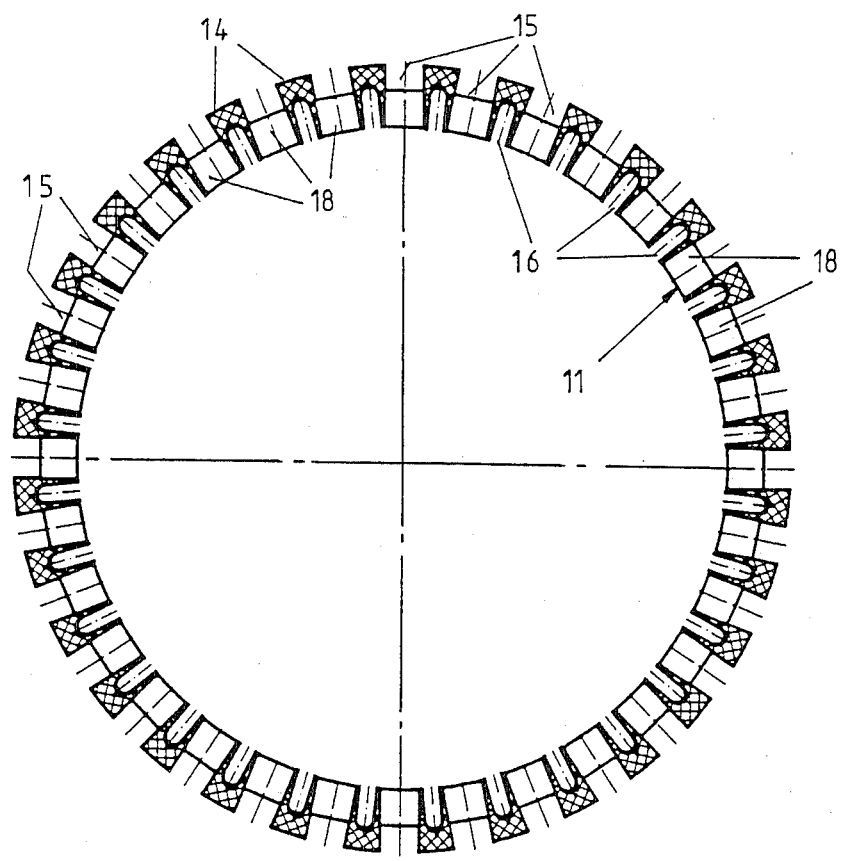
FIG. 3 is a cross-sectional view taken along the line III—III in FIG. 2.
Figure 4:
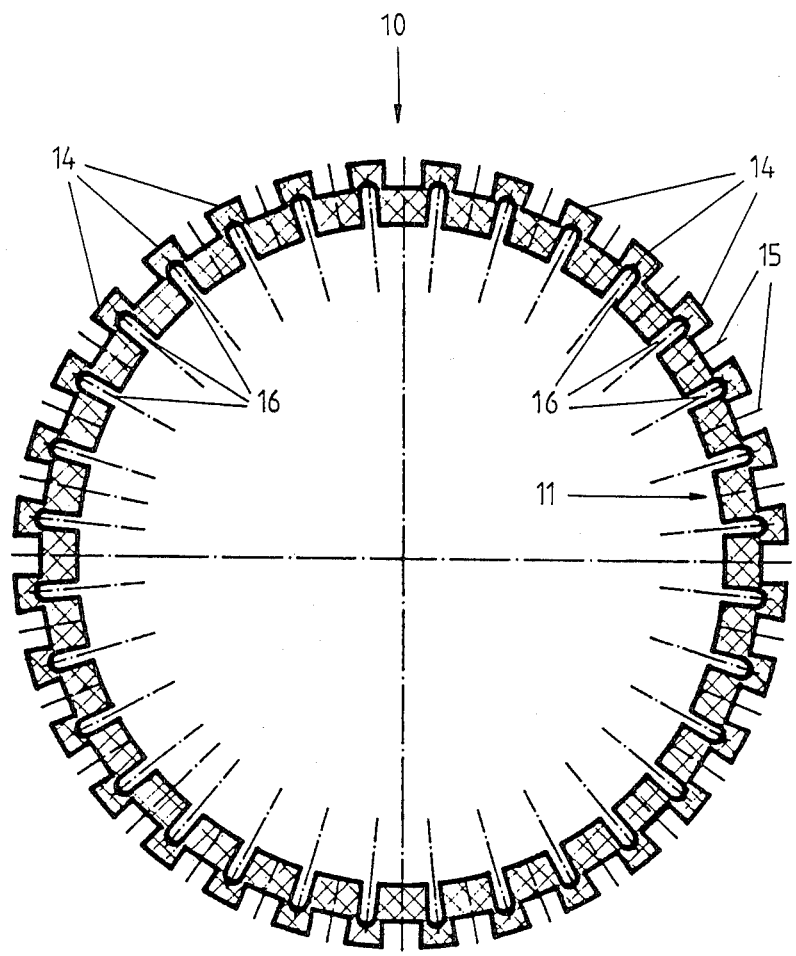
FIG. 4 is a cross-sectional view taken along the line IV—IV in FIG. 2.

As show in FIGS. 3 and 4, the hose-like portion 11 of sleeve 10 has a profile with protuberances 14 and depressions 15, which are constructed as groove-like cavities. On the inside of the sleeve in the vicinity of protuberances 14, there are also narrower grooves 16, so that considered circumferentially a type of concertina profile is obtained. The protuberances 14 are located on a common envelope surface shaped like a circular cylinder, whose external diameter in the relaxed position is somewhat larger than the internal diameter of the pipeline (FIG. 1), so that after inserting the scraper in the pipeline, the sleeve 10 is compressed somewhat. This ensures that the protuberances 14 thereof engage on the pipe wall.

The sensors 17, used for measurement or nonedestructive testing, are located in depressions 15 (FIG. 2). For this purpose, in the vicinity of depressions 15, sleeve 10 has through-holes 18, in which the sensors 17 are inserted. Threaded bushes 19 are cast in the area between holes 18 for fixing sensors 17. Sensors 17 are connected by connecting cables 21 to the test electronics on the pressure-tight casing of scraper body 4 (FIG. 1).

Figure 5:
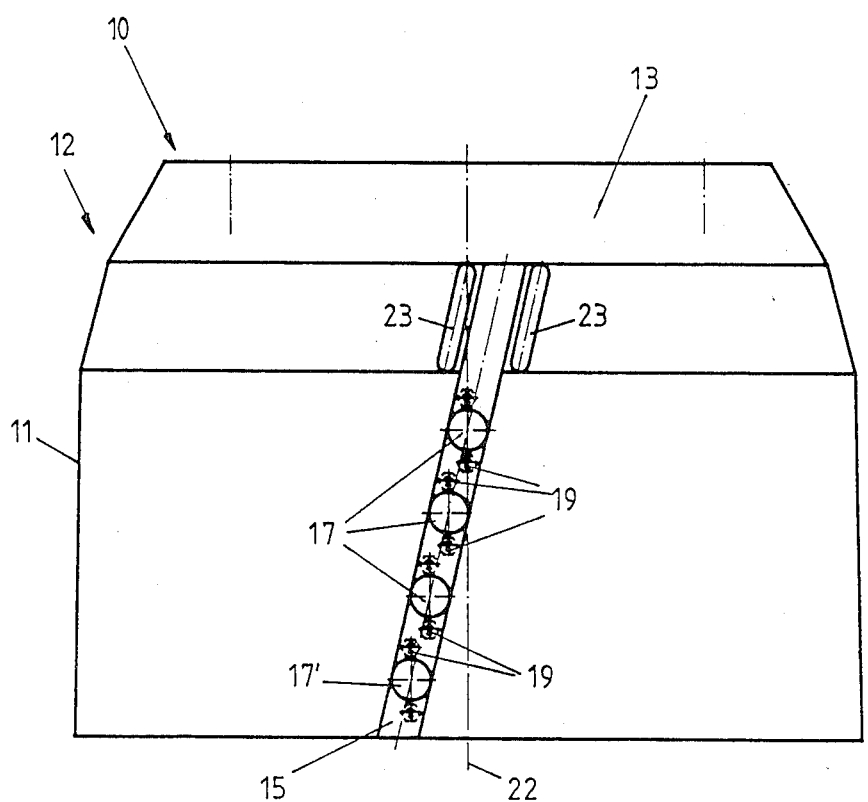
FIG. 5 is a view of the sleeve.

As shown in FIG. 5, the grooves 15 are at an acute angle to axis 22 of sleeve 10. Several sensors 17 are successively arranged in each groove 15, only one being shown in FIG. 5. The sensors 17 are spaced in such a way that there is an overlap in the axial direction of their effective areas. In addition, the length of groove 15 and the number of sensors 17 are such that the effective area of the last sensor in one groove overlaps with the affective area of the first sensor in the adjacent groove, so that the effective areas of the sensors completely cover the pipe walls.

Figure 7:
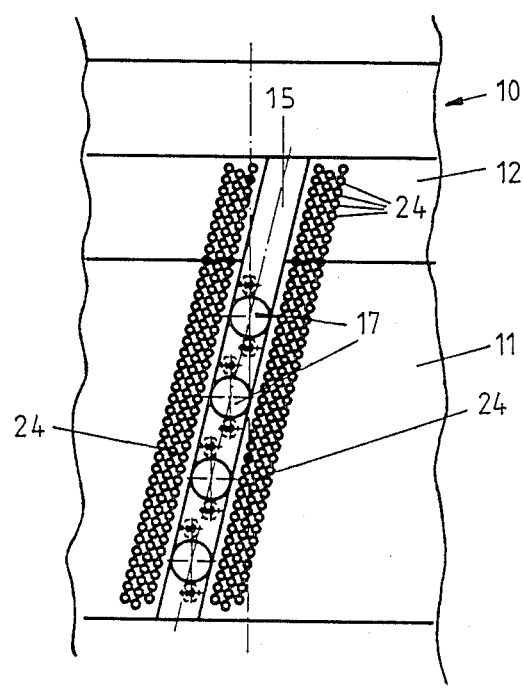
FIG. 7 is a partial view of the sleeve in a different construction.

As stated, the sleeve 10 is made from a rubber elastic material. The deformability of the sleeve 10 is further aided by its special profile (FIGS. 3 and 4). Despite the elasticity of the sleeve 10, it is ensured that the effective areas of the sensor 17 located in holes 18 are located on a cylindrical base surface, so that all the sensors 17 have the same, constant spacing with respect to the pipe wall. In order to also ensure elasticity in the front region, the outer grooves extend into the vicinity of the conical portion, while the inner grooves 16 extend up to the inside of support flange 13. Slot-like recesses 23 (FIGS. 2 and 5) can be provided in the transition region between portion 11 and conical portion 12 and run parallel to grooves 15. A construction modified compared with FIGS. 2 to 4 for obtaining an adequate elasticity of sleeve 10 is shown in FIG. 7. There are once again grooves 15, as in the previously described embodiment, while the inner grooves 16 (FIGS. 2 and 3) have been replaced by a narrow pattern of small diameter holes 24. Thus, once again sleeve 10 can be circumferentially compressed and expanded.

Figure 6:
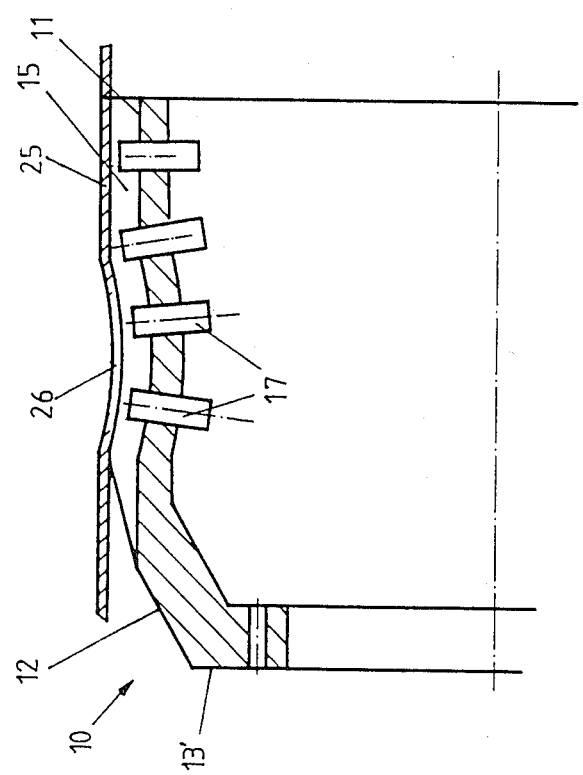
FIG. 6 is a partial longitudinal section through the sleeve in an operating position.

The elasticity of the sleeve 10 resulting from the characteristics of the material and the profiling, occurs not only circumferentially, but also longitudinally. Thus, the sleeve 10 is both circumferentially and axially adapted to the pipe wall, as is in particular indicated in FIG. 6, where the pipe wall 25 has a bulge 26 or an annular constriction. Sleeve 10 is drawn in or necked at the corresponding point, but it is ensured that the sensors 17 maintain the same spacing and angular position with respect to the deformed wall portion 26.

Figure 8:
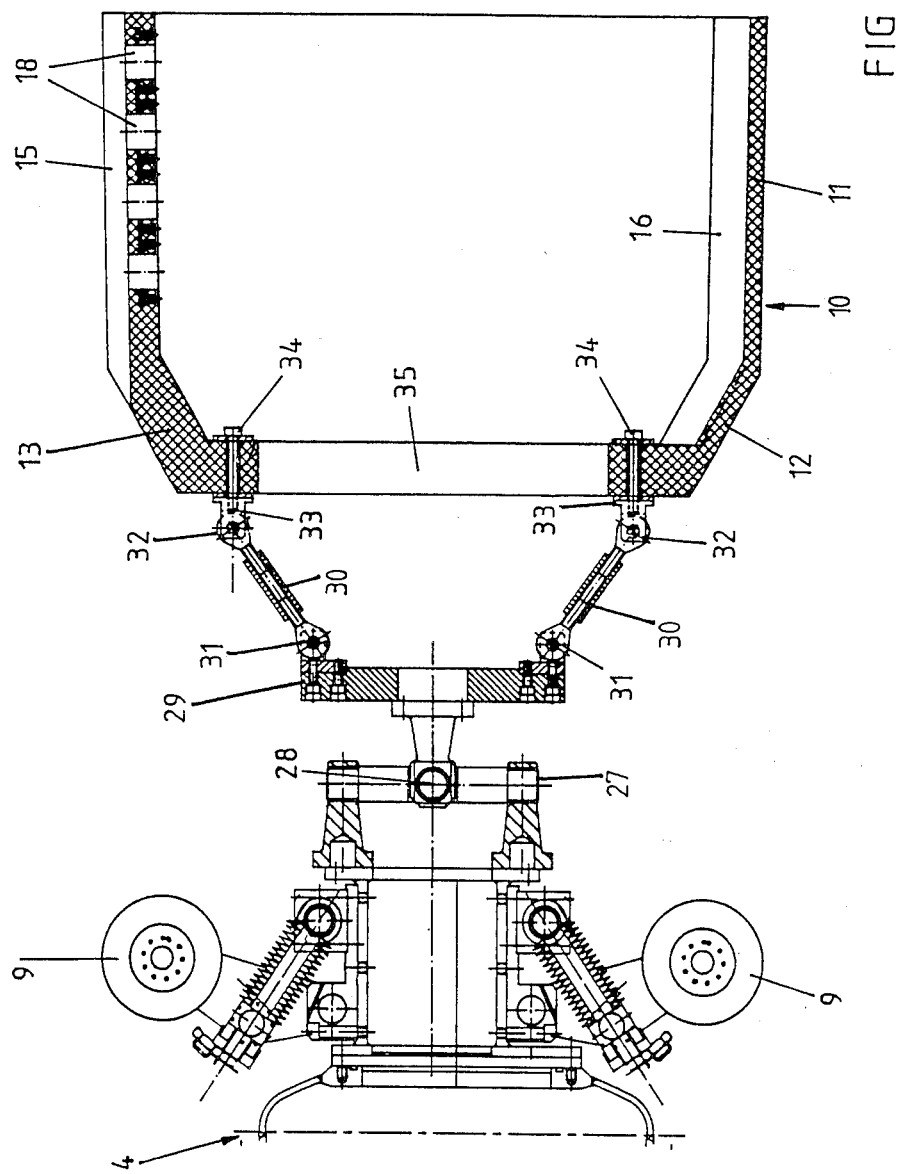
FIG. 8 is a larger-scale partial view of the connection of the sleeve to the scraper.

FIG. 8 shows in greater detail the coupling of sleeve 10 to the last scraper body 4, having in the vicinity of the last guide roller set 9 a support plate 27. An intermediate plate 29 is coupled by a universal joint 28 to support plate 27. Sleeve 10 is attached by tie rods 30 to intermediate plate 29. Both ends of the tie rods are articulated by ball and socket joints 31, 32 to intermediate plate 29 or bearing blocks 33, which are fixed to the support flange 13 of sleeve 10 by cotter pins 34. Finally, sleeve 10 provided in the center of support flange 13 with a large area recess 35, so as to permit the free through-flow of the transported medium.

As can be gathered from FIG. 8, the tie rods 30 are arranged obliquely, preferably in such a way that they are roughly in the conical surface defined by the conical portion 12 of sleeve 10 or parallel thereto.

What is claimed is:

1. An apparatus, for the measurement and non-destructive material testing of laid pipelines including a scraper moved through the pipeline and guided on an inner wall thereof and at least one circular support with sensors arranged on a circumference thereof and at least one pressure-tight casing, which receives devices for processing and recording measured values and for a power supply, therein the support is constructed as a cylindrical sleeve of a rubber elastic material and is provided with an axially, radially and circumferentially regular profile, and protuberances located on a cylindrical envelope surface with a somewhat larger external diameter than the internal diameter of the pipeline, and depressions provided for containing the sensors on surface concentric to the envelope surface, and wherein the protuberances and depressions extend in a direction substantially axially parallel to a longitudinal axis of the cylindrical sleeve.

2. An apparatus according to claim 1, wherein the depressions are formed by grooves in the cylindrical sleeve.

3. An apparatus according to claim 1, wherein the cylindrical sleeve is internally provided with substantially axially parallel grooves in the vicinity of the protuberances.

4. An apparatus according to claim 1, wherein the vicinity of the protuberances, the sleeve is provided with a narrow pattern of small diameter holes.

5. An apparatus according to claim 1, wherein the protuberances and said depressions are at an acute angle with respect to the longitudinal axis of the cylindrical sleeve.

6. An apparatus according to claim 5, wherein the acute angle between the depressions and the longitudinal axis of the cylindrical sleeve is such that the effective areas of the sensors successively arranged in the depression overlap one another in the axial direction.

7. An apparatus according to claim 6, wherein the length of the depressions is such that the effective areas of the last sensor in one of the depressions and those of the first sensor in the adjacent depression overlap one another.

8. An apparatus according to claim 1, wherein the sleeve has threaded bushes open towards the inside for fixing the sensors.

9. An apparatus according to claim 4, wherein threaded bushes are arranged in portions of the sleeve forming the depressions between the holes receiving the sensors.

10. An apparatus according to claim 1, wherein the leading end of the sleeve in the direction of movement of the scraper is conically drawn inwards to a support flange by means of which it is fixed to the scraper.

11. An apparatus, according to claim 1, wherein a universal joint means is provided for connecting the sleeve to the scraper.

12. An apparatus according to claim 11, wherein the sleeve is attached to a trailing end of the scraper, as viewed in a direction of movement.

13. An apparatus according to claim 11, wherein the universal joint means is positioned at a limited distance behind guide rollers engaging on the pipe wall provided at the trailing end of the scraper.

14. An apparatus according to claim 11, wherein several tie rods are distributed about the longitudinal axis of the cylindrical sleeve and spherically mounted at both ends, and disposed between the universal joint means and the support flange for the cylindrical sleeve.

15. An apparatus according to claim 15, wherein the tie rods ends facing the scraper are spherically mounted on an intermediate plate means carrying the universal joint means.

16. An apparatus according to claim 15, wherein the tie rods slope outwards from the intermediate plate.

17. An apparatus according to claims 16, wherein the sloping tie rods are located in the extension of an inwardly drawn conical surface.

* * * * *